(12) United States Patent
Eberl et al.

(10) Patent No.: US 7,549,988 B2
(45) Date of Patent: Jun. 23, 2009

(54) HYBRID LESION FORMATION APPARATUS, SYSTEMS AND METHODS

(75) Inventors: Greg Eberl, Sunnyvale, CA (US); David K. Swanson, Campbell, CA (US); Huy D. Phan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 456 days.

(21) Appl. No.: 10/930,073

(22) Filed: Aug. 30, 2004

(65) Prior Publication Data

US 2006/0047277 A1 Mar. 2, 2006

(51) Int. Cl.
*A61B 18/18* (2006.01)

(52) U.S. Cl. .......................................... 606/41; 606/51
(58) Field of Classification Search ................... 606/41, 606/45–52
See application file for complete search history.

(56) References Cited

U.S. PATENT DOCUMENTS

| | | | |
|---|---|---|---|
| 4,011,872 A | 3/1977 | Komiya | |
| 4,685,459 A | 8/1987 | Koch | |
| 5,190,541 A * | 3/1993 | Abele et al. | 606/46 |
| 5,342,359 A * | 8/1994 | Rydell | 606/51 |
| 5,364,395 A * | 11/1994 | West, Jr. | 606/46 |
| 5,398,683 A | 3/1995 | Edwards et al. | |
| 5,450,846 A | 9/1995 | Goldreyer | |
| 5,545,193 A | 8/1996 | Fleischman et al. | |
| 5,546,682 A | 8/1996 | Skerry | |
| 5,575,810 A | 11/1996 | Swanson et al. | |
| 5,582,609 A | 12/1996 | Swanson et al. | |
| 5,630,426 A | 5/1997 | Eggers et al. | |
| 5,637,090 A | 6/1997 | McGee et al. | |
| 5,673,695 A | 10/1997 | McGee | |
| 5,697,882 A | 12/1997 | Eggers et al. | |
| 5,755,715 A | 5/1998 | Stern et al. | |
| 5,755,760 A | 5/1998 | Maguire et al. | |
| 5,782,899 A | 7/1998 | Imran | |
| 5,788,688 A | 8/1998 | Bauer et al. | |
| 5,797,905 A | 8/1998 | Fleischman et al. | |
| 5,824,005 A | 10/1998 | Motamedi et al. | |
| 5,837,001 A | 11/1998 | Mackey | |
| 5,904,681 A * | 5/1999 | West, Jr. | 606/41 |
| 5,938,694 A | 8/1999 | Jaraczewski et al. | |
| 5,944,718 A * | 8/1999 | Austin et al. | 606/48 |
| 5,961,513 A | 10/1999 | Swanson et al. | |
| 5,971,983 A | 10/1999 | Lesh | |
| 5,980,519 A | 11/1999 | Hahnen et al. | |

(Continued)

FOREIGN PATENT DOCUMENTS

| | | |
|---|---|---|
| DE | 4116970 A1 | 11/1992 |
| EP | 0694291 A1 | 7/1995 |
| EP | 1557129 A1 | 8/1996 |
| EP | 0856291 A2 | 1/1998 |
| EP | 1125549 A2 | 2/2001 |
| WO | WO 01/72234 A1 | 10/2001 |

OTHER PUBLICATIONS

PCT International Search Report dated Dec. 1, 2005 for corresponding PCT App. Ser. No. PCT/US05/028515.

(Continued)

*Primary Examiner*—Michael Peffley
(74) *Attorney, Agent, or Firm*—Vista IP Law Group LLP

(57) ABSTRACT

A hybrid lesion formation apparatus including a surgical probe component and clamp component that share a common electrical connector.

47 Claims, 5 Drawing Sheets

U.S. PATENT DOCUMENTS

| | | | |
|---|---|---|---|
| 6,004,269 | A | 12/1999 | Crowley et al. |
| 6,010,500 | A | 1/2000 | Sherman et al. |
| 6,017,358 | A * | 1/2000 | Yoon et al. .................. 606/205 |
| 6,023,638 | A | 2/2000 | Swanson |
| 6,050,996 | A | 4/2000 | Schmaltz et al. |
| 6,056,747 | A | 5/2000 | Saadat et al. |
| 6,063,080 | A | 5/2000 | Nelson et al. |
| 6,096,037 | A | 8/2000 | Mulier et al. |
| 6,113,596 | A | 9/2000 | Hooven et al. |
| 6,115,626 | A | 9/2000 | Whayne et al. |
| 6,142,994 | A | 11/2000 | Swanson et al. |
| 6,171,305 | B1 | 1/2001 | Sherman |
| 6,183,468 | B1 | 2/2001 | Swanson et al. |
| 6,190,381 | B1 | 2/2001 | Olsen et al. |
| 6,224,593 | B1 | 5/2001 | Ryan et al. |
| 6,237,605 | B1 * | 5/2001 | Vaska et al. .................. 128/898 |
| 6,245,068 | B1 | 6/2001 | Olson et al. |
| 6,267,761 | B1 * | 7/2001 | Ryan ........................... 606/50 |
| 6,273,887 | B1 | 8/2001 | Yamauchi et al. |
| 6,277,117 | B1 | 8/2001 | Tetzlaff et al. |
| 6,286,512 | B1 | 9/2001 | Loeb et al. |
| 6,308,104 | B1 | 10/2001 | Taylor et al. |
| 6,311,692 | B1 | 11/2001 | Vaska et al. |
| 6,312,425 | B1 | 11/2001 | Simpson et al. |
| 6,314,962 | B1 | 11/2001 | Vaska et al. |
| 6,325,797 | B1 | 12/2001 | Stewart et al. |
| 6,464,700 | B1 | 10/2002 | Koblish et al. |
| 6,468,272 | B1 | 10/2002 | Koblish et al. |
| 6,471,699 | B1 | 10/2002 | Fleischman et al. |
| 6,488,680 | B1 | 12/2002 | Francischelli et al. |
| 6,522,905 | B2 | 2/2003 | Desai |
| 6,529,756 | B1 | 3/2003 | Phan et al. |
| 6,542,781 | B1 | 4/2003 | Koblish et al. |
| 6,558,408 | B1 | 5/2003 | Fogarty et al. |
| 6,584,360 | B2 | 6/2003 | Francischelli et al. |
| 6,616,661 | B2 * | 9/2003 | Wellman et al. .............. 606/50 |
| 6,645,202 | B1 | 11/2003 | Pless et al. |
| 6,692,491 | B1 * | 2/2004 | Phan ........................... 606/41 |
| 6,699,240 | B2 * | 3/2004 | Francischelli ................ 606/32 |
| 6,706,038 | B2 | 3/2004 | Francischelli et al. |
| 6,771,996 | B2 | 8/2004 | Bowe et al. |
| 6,889,694 | B2 | 5/2005 | Hooven |
| 2001/0001314 | A1 | 5/2001 | Davison |
| 2001/0012918 | A1 | 8/2001 | Swanson |
| 2001/0025177 | A1 | 9/2001 | Woloszko |
| 2002/0002372 | A1 | 1/2002 | Jahns |
| 2002/0026187 | A1 | 2/2002 | Swanson |
| 2002/0099428 | A1 | 7/2002 | Kaufman |
| 2002/0120267 | A1 | 8/2002 | Phan |
| 2003/0097126 | A1 | 5/2003 | Woloszko |
| 2003/0158547 | A1 | 8/2003 | Phan |
| 2003/0158549 | A1 | 8/2003 | Swanson |
| 2003/0212444 | A1 | 11/2003 | Truckai |
| 2004/0059325 | A1 | 3/2004 | Swanson |
| 2004/0097117 | A1 | 5/2004 | Gonnering |
| 2004/0186467 | A1 | 9/2004 | Swanson |
| 2005/0019545 | A1 | 1/2005 | Riebel |
| 2005/0019653 | A1 | 1/2005 | Dahlberg |
| 2005/0119648 | A1 | 6/2005 | Swanson |
| 2005/0119649 | A1 | 6/2005 | Swanson |
| 2005/0119654 | A1 | 6/2005 | Swanson |
| 2005/0203499 | A1 | 9/2005 | Pendekanti |
| 2006/0047277 | A1 | 3/2006 | Eberl |
| 2006/0100619 | A1 * | 5/2006 | McClurken et al. ........... 606/45 |
| 2006/0195081 | A1 | 8/2006 | Landis et al. |

OTHER PUBLICATIONS

Amendment dated Jan. 24, 2008 for U.S. Appl. No. 10/255,025, filed Sep. 24, 2002 (16 pages).
Non-Final Office Action dated Sep. 24, 2007 for U.S. Appl. No. 10/255,025, filed Sep. 24, 2002 (6 pages).
Notice of Allowance dated May 10, 2006 for U.S. Appl. No. 10/255,025, filed Sep. 24, 2002 (4 pages).
Amendment dated Apr. 28, 2006 for U.S. Appl. No. 10/255,025, filed Sep. 24, 2002 (8 pages).
Final Office Action dated Feb. 14, 2006 for U.S. Appl. No. 10/255,025, filed Sep. 24, 2002 (11 pages).
Amendment dated Dec. 3, 2005 for U.S. Appl. No. 10/255,025, filed Sep. 24, 2002 (19 pages).
Declaration of Dr. David K. Swanson Under §132 dated Nov. 22, 2005 for U.S. Appl. No. 10/255,025, filed Sep. 24, 2002 (3 pages).
Non-Final Office Action dated Jul. 13, 2005 for U.S. Appl. No. 10/255,025, filed Sep. 24, 2002 (9 pages).
Advisory Action dated Apr. 11, 2005 for U.S. Appl. No. 10/255,025, filed Sep. 24, 2002 (2 pages).
Amendment dated Mar. 14, 2005 for U.S. Appl. No. 10/255,025, filed Sep. 24, 2002 (20 pages).
Final Office Action dated Dec. 7, 2004 for U.S. Appl. No. 10/255,025, filed Sep. 24, 2002 (10 pages).
Amendment dated Sep. 28, 2004 for U.S. Appl. No. 10/255,025, filed Sep. 24, 2002 (16 pages).
Non-Final Office Action dated Jul. 19, 2004 for U.S. Appl. No. 10/255,025, filed Sep. 24, 2002 (8 pages).
International Search Report dated Jan. 12, 2004 for PCT/US 03/29270, filed Sep. 24, 2002 (10 pages).
Amendment dated Oct. 15, 2007 for U.S. Appl. No. 10/727,143, filed Dec. 2, 2003 (13 pages).
Non-Final Office Action dated Jun. 15, 2007 for U.S. Appl. No. 10/727,143, filed Dec. 2, 2003 (9 pages).
Amendment dated Apr. 26, 2007 for U.S. Appl. No. 10/727,143, filed Dec. 2, 2003 (12 pages).
Final Office Action dated Feb. 1, 2007 for U.S. Appl. No. 10/727,143, filed Dec. 2, 2003 (8 pages).
Amendment dated Nov. 22, 2006 for U.S. Appl. No. 10/727,143, filed Dec. 2, 2003 (12 pages).
Non-Final Office Action dated Aug. 18, 2006 for U.S. Appl. No. 10/727,143, filed Dec. 2, 2003 (8 pages).
PCT International Search Report dated Apr. 7, 2005 for PCT/US2004/039282 (4 pages).
PCT Written Opinion dated Apr. 7, 2005, for International Application No. PCT/US2004/39282 (7 pages).
PCT International Preliminary Examination Report on Patentability dated Jun. 7, 2006 for PCT/US2004/39282 (8 pages).
PCT Written Opinion dated Dec. 1, 2005, for International Application No. PCT/US2005/028515 (6 pages).
PCT International Preliminary Examination Report on Patentability dated Mar. 8, 2007 for PCT/US2004/028515 (7 pages).
(02-0298EP01) Communication under Rule 51(4) EPC, for EP application No. 03756823.5, dated Aug. 8, 200gApplicant Boston Scientific Scimed, (6 pages).
(02-0298EP01) Communication of a Notice of Opposition for EP application No. 03756823.5, dated Nov. 29, 2006, Applicant Boston Scientific Scimed, (15 pages).
(02-0298EP01) Response to Notice of Opposition for EP application No. 03756823.5, dated Jun. 19, 2007, Applicant Boston Scientific Scimed, (8 pages).
EPO Communication issued Mar. 18, 2008 for EP Patent Application No. 03756823.5 (now EP Patent No. 1542604), Applicant: Boston Scientfic Limited; with Letter of Opposition from Hoffman Eitle dated Mar. 11, 2008 (6 pages).
Communication Pursuant to Article 96(2) EPC dated Nov. 14, 2007 for EP Patent Application No. 05784208.0, Applicant: Boston Scientific Scimed (3 pages).
Office Action dated Mar. 27, 2008 for related U.S. Appl. No. 10/727,143, filed Dec. 2, 2003, Inventor: David K. Swanson (9 pages).
Amendment dated May 21, 2008 for related U.S. Appl. No. 10/727,143, filed Dec. 2, 2003, Inventor: David K. Swanson (17 pages).
Office Action dated Jun. 12, 2008 for related U.S. Appl. No. 10/727,143, filed Dec. 2, 2003, Inventor: David K. Swanson (9 pages).

Office Action dated Mar. 31, 2008 for related U.S. Appl. No. 10/255,025, filed Sep. 24, 2002, Inventor: David K. Swanson (10 pages).

Amendment dated Jun. 26, 2008 for related U.S. Appl. No. 10/255,025, filed Sep. 24, 2002, Inventor: David K. Swanson (23 pages).

Response dated Feb. 22, 2008 for related U.S. Appl. No. 11/110,149, filed Apr. 20, 2005, Inventor: William Landis (6 pages).

Office Action dated May 20, 2008 for related U.S. Appl. No. 11/110,149, filed Apr. 20, 2005, Inventor: William Landis (11 pages).

* cited by examiner

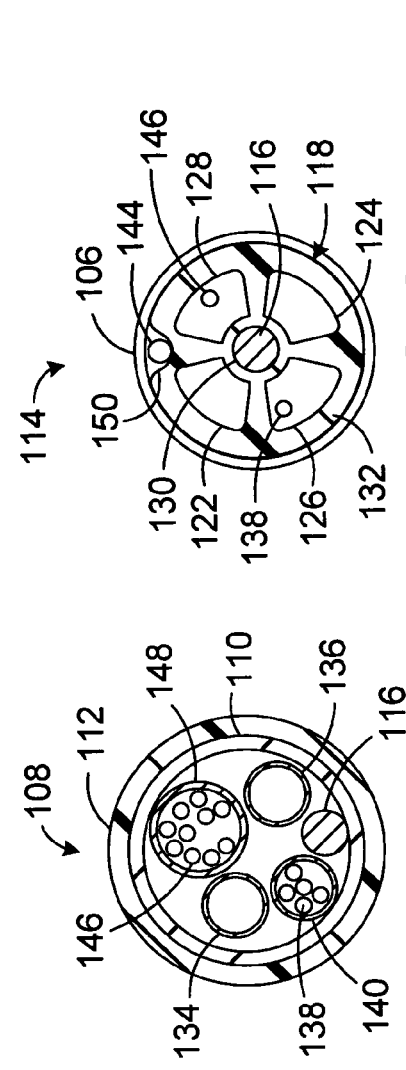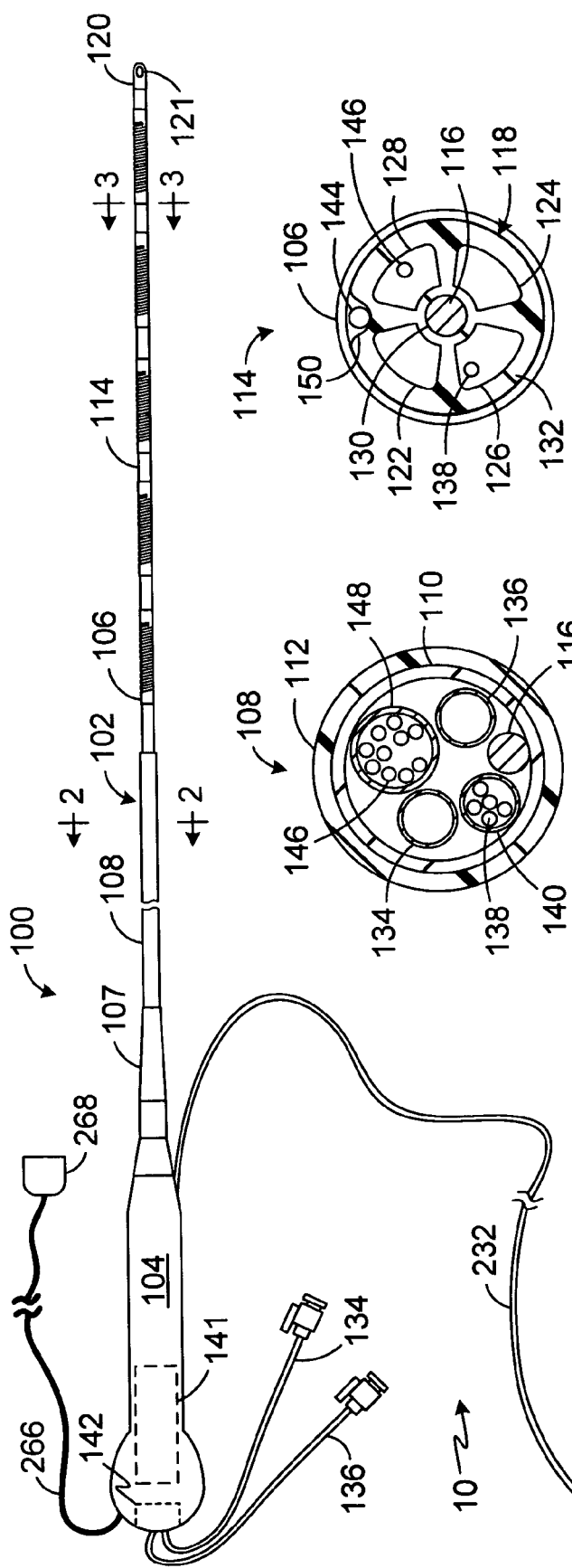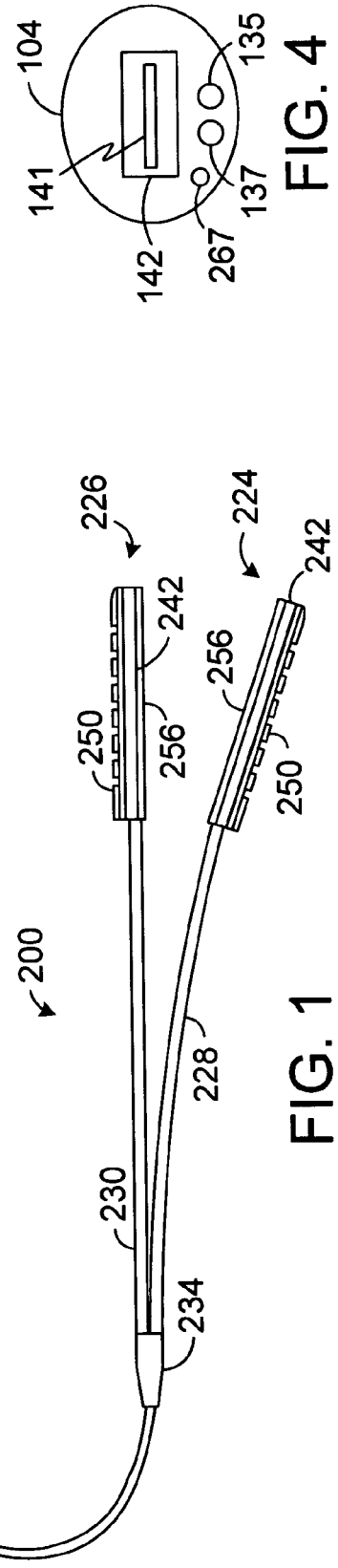

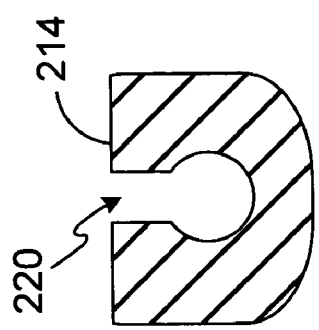
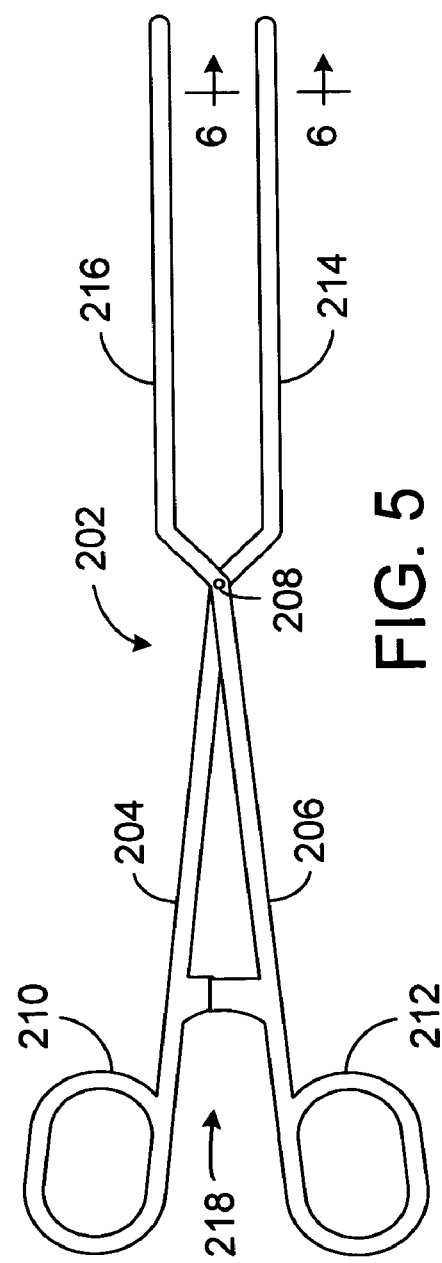
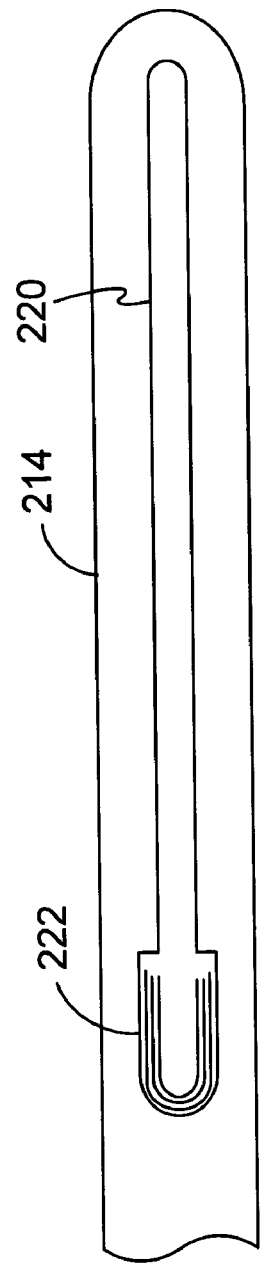
FIG. 6
FIG. 5
FIG. 7

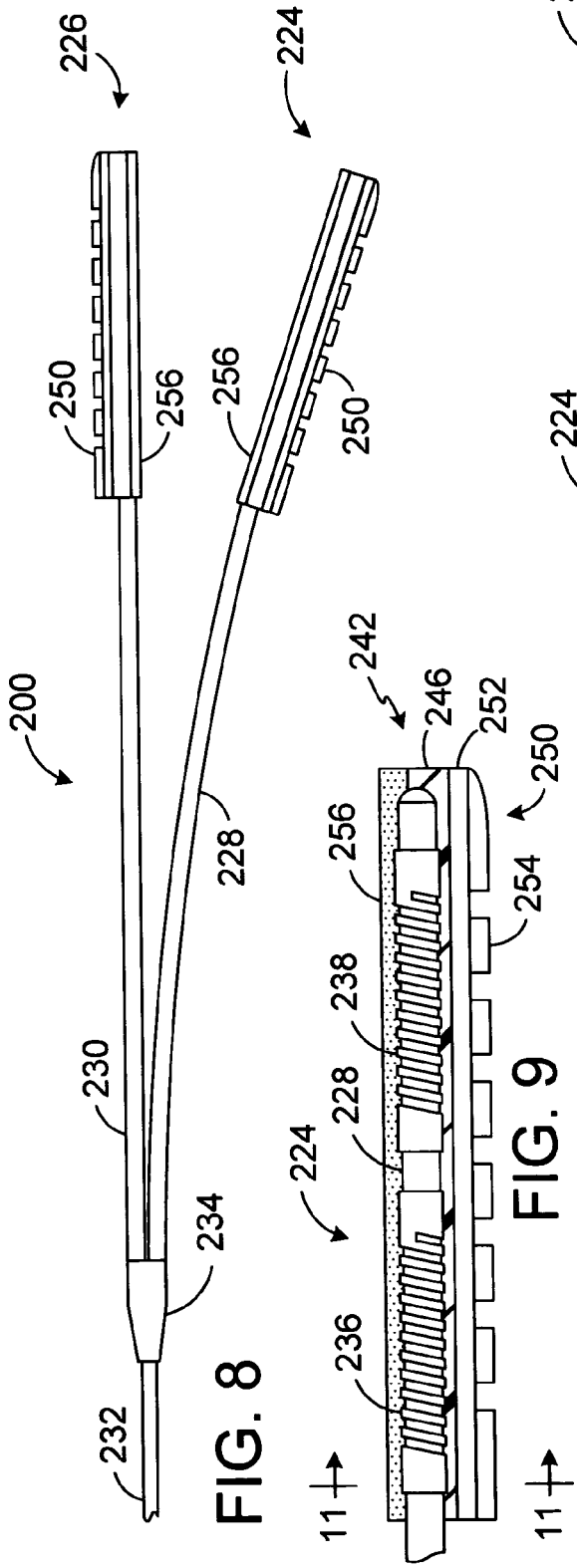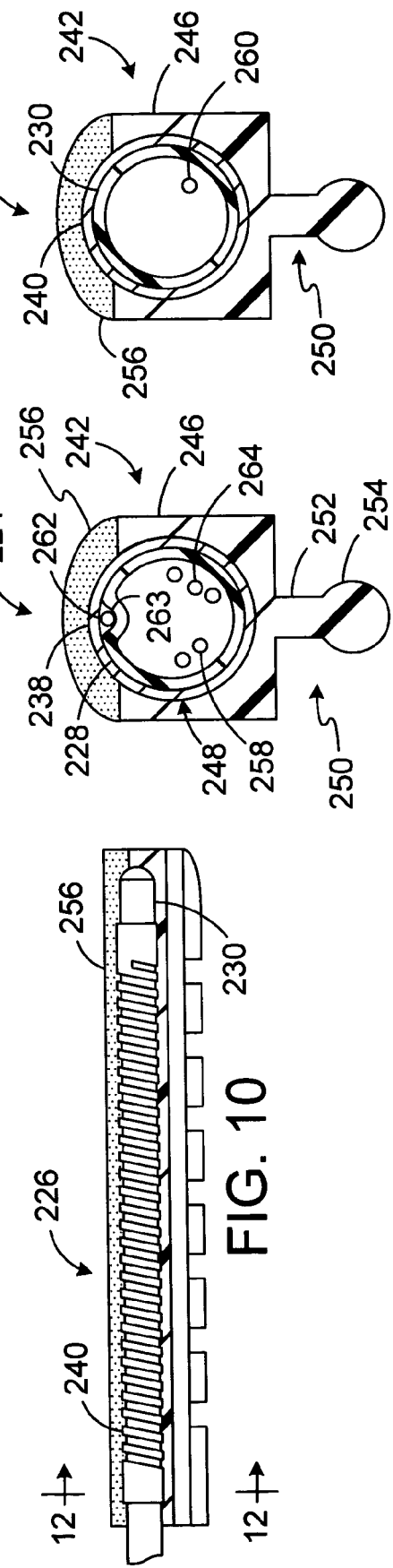

HYBRID LESION FORMATION APPARATUS, SYSTEMS AND METHODS

BACKGROUND OF THE INVENTIONS

1. Field of Inventions

The present inventions relate generally to devices for performing therapeutic operations on body tissue.

2. Description of the Related Art

There are many instances where electrophysiology devices are used to form therapeutic lesions in tissue. Therapeutic lesions are frequently formed to treat conditions in the heart, prostate, liver, brain, gall bladder, uterus, breasts, lungs and other solid organs. Electromagnetic radio frequency ("RF") may, for example, be used to heat and eventually kill (i.e. "ablate") tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

The tissue coagulation energy is typically supplied by an electrosurgical unit ("ESU") during the therapeutic procedure. More specifically, after an electrophysiology catheter, surgical probe or clamp has been connected to the ESU, and the electrodes or other energy transmission elements on the catheter, surgical probe or clamp have been positioned adjacent to the target tissue, energy from the ESU is transmitted through the energy transmission elements to the tissue to from a lesion. The amount of power required to coagulate tissue ranges from 5 to 150 W.

Some electrophysiology procedures require the use of more than one electrophysiology device. One example of such a procedure involves the formation of therapeutic lesions to the treat cardiac conditions such as atrial fibrillation. Here, a clamp may be used to create a first transmural epicardial lesion around the right pulmonary vein pair and a second transmural epicardial lesion around the left pulmonary vein pair. Thereafter, if needed, a surgical probe may be used to create a linear transmural epicardial lesion between the right and left pulmonary vein pairs. A linear transmural lesion that extends from the lesion between the right and left pulmonary vein pairs to the left atrial appendage may also be created.

The present inventors have determined that conventional lesion formation devices are susceptible to improvement. For example, the present inventors have determined that the aforementioned procedure is inconvenient because it requires the surgical staff to disconnect the clamp from the ESU and connect the surgical probe to the ESU during the procedure. The inconvenience is compounded in those instances where the ESU resets and performs a diagnostic procedure each time a device is connected thereto. The present inventors have also determined that there may be more efficient and cost effective ways, in terms of materials, manufacturing, sterilization, shipping, etc., to provide physicians with the capabilities of two separate devices, such as the aforementioned separate clamp and surgical probe.

SUMMARY OF THE INVENTIONS

An apparatus in accordance with one invention herein includes a probe component including at least one energy transmission device and an electrical connector operably connected to the at least one energy transmission device and a clamp component including at least one energy transmission device operably connected to the probe component electrical connector.

A lesion formation apparatus in accordance with one invention herein includes a tissue coagulation probe including an energy transmission device carried, a bipolar tissue coagulation device including first and second energy transmission devices, a first connector that facilitates connection of the energy transmission device on the tissue coagulation probe and the first energy transmission device on the bipolar tissue coagulation device to a power output port, and a second connector that connects the second energy transmission device on the bipolar tissue coagulation device to a power return port.

A system in accordance with one invention herein includes a source of tissue coagulation energy and a lesion formation apparatus including a probe component and a clamp component.

A method in accordance with one invention herein includes the step of simultaneously connecting a tissue coagulation probe and a clamp-based tissue coagulation device to the same power output port on a source of tissue coagulation energy.

BRIEF DESCRIPTION OF THE DRAWINGS

Detailed description of preferred embodiments of the inventions will be made with reference to the accompanying drawings.

FIG. 1 is a plan view of a hybrid lesion formation apparatus in accordance with a preferred embodiment of a present invention.

FIG. 2 is a section view taken along line 2-2 in FIG. 1.

FIG. 3 is a section view taken along line 3-3 in FIG. 1.

FIG. 4 is an end view of the handle illustrated in FIG. 1.

FIG. 5 is a plan view of a clamp in accordance with a preferred embodiment of a present invention.

FIG. 6 is a section view taken along line 6-6 in FIG. 5.

FIG. 7 is a top view of a portion of the clamp illustrated in FIG. 5.

FIG. 8 is a plan view of a clamp component in accordance with a preferred embodiment of a present invention.

FIG. 9 is a side, partial section view of a portion of the clamp component illustrated in FIG. 8.

FIG. 10 is a side, partial section view of a portion of the clamp component illustrated in FIG. 8.

FIG. 11 is a section view taken along line 11-11 in FIG. 9.

FIG. 12 is a section view taken along line 12-12 in FIG. 10.

DETAILED DESCRIPTION OF THE PREFERRED EMBODIMENTS

Figure 13:
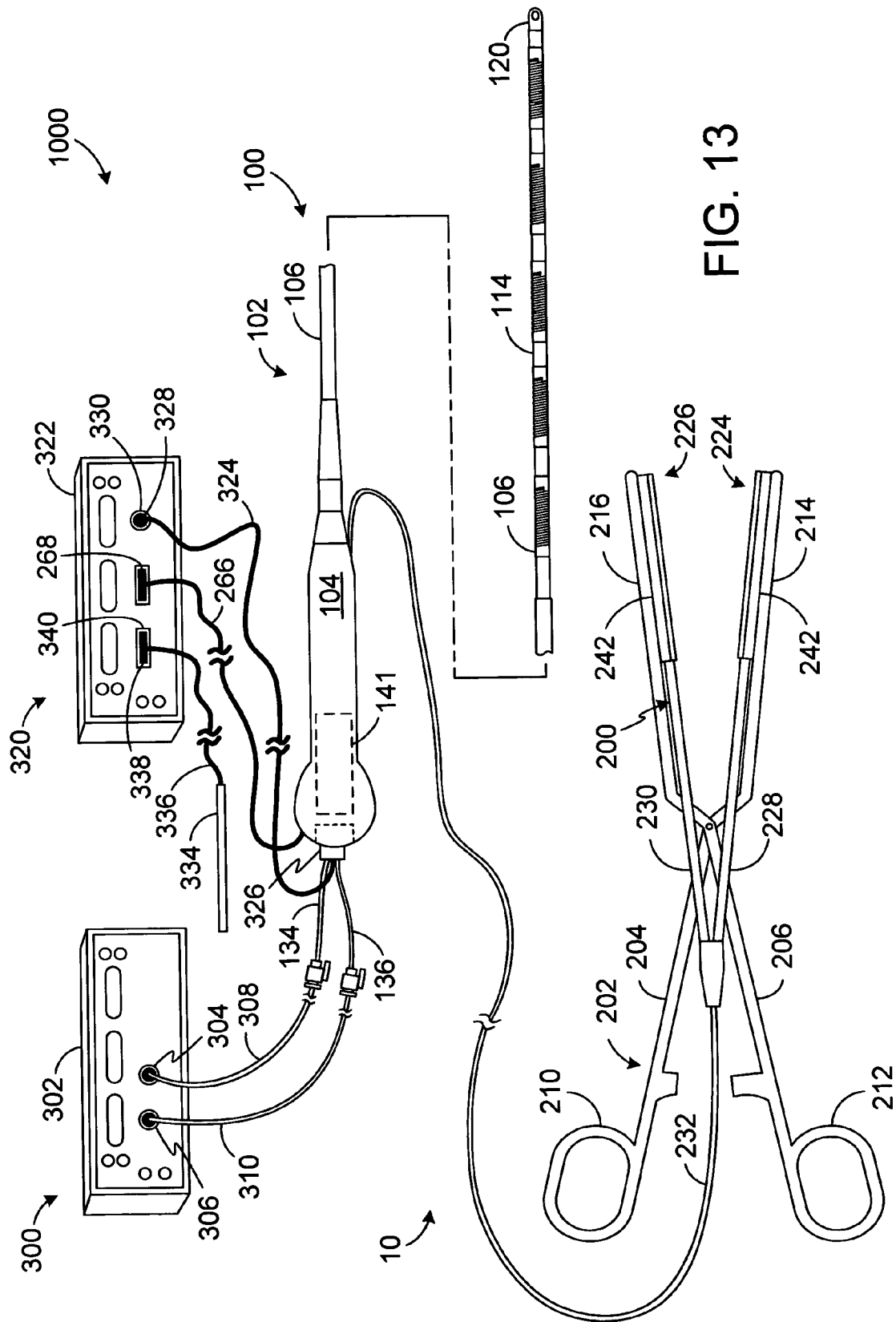
FIG. 13 is a perspective view of a surgical system in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction

II. Exemplary Hybrid Lesion Formation Apparatus

III. Exemplary Systems

The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, and other solid organs.

II. Exemplary Hybrid Lesion Formation Apparatus

A hybrid lesion formation apparatus in accordance with one embodiment of a present invention is generally represented by reference numeral 10 in FIG. 1. The exemplary embodiment includes a surgical probe component 100 and a clamp component 200. The clamp component 200 in the exemplary embodiment is adapted to be removably secured to a clamp so as to convert a conventional clamp into a electrophysiology device that may be used to form lesions in the manner discussed in greater detail below. Alternatively, in other implementations, the clamp component may include the clamp itself. The surgical probe component 100 and clamp component 200 preferably share a common electrical connector which may be used to connect the hybrid lesion formation apparatus 10 to an electrosurgical unit ("ESU") in the manner described below with reference to FIG. 13.

There are a variety of advantages associated with such a device. By way of example, but not limitation, providing a surgical probe component 100 and a clamp component 200 in a single device facilitates the use of a single handle (and associated electrical connectors). A conventional surgical system including a surgical probe and a clamp would have two handles. In addition to cost savings, the use of a single handle (and associated electrical connectors) allows the physician to avoid the inconveniences associated with disconnecting one device from an ESU and connecting another during a surgical procedure. The sterilization, packaging and shipment of the present hybrid lesion formation apparatus may also be accomplished in a manner that is more efficient than the sterilization, packaging and shipment of separate devices.

Referring to FIGS. 1-4, the surgical probe component 100 in the exemplary implementation includes a relatively short shaft 102, a handle 104 that is secured to the shaft, and one or more electrodes 106 or other energy transmission devices on the distal portion of the shaft. A strain relief element 107 may also be provided. The shaft 102 is preferably, although not necessarily, about 13 cm to 51 cm in length, and most preferably about 20 cm to 30 cm in length. The shaft 102 is also preferably relatively stiff. In other words, the shaft 102 is rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

In the exemplary implementation illustrated in FIGS. 1-4, the shaft 102 consists of a proximal portion 108, including a malleable hypotube 110 and a non-conductive outer polymer coating 112, and distal portion 114, including a malleable mandrel 116 and a multi-lumen electrically non-conductive outer structure 118. The proximal portion 108 will typically be about 15 to 40 cm in length, while the distal portion will typically be about 6 to 15 cm in length. The proximal end of the malleable mandrel 116 is secured to the inner surface of the distal end of the hypotube 110 by, for example, soldering, spot welding or adhesives. Mechanical methods, such as crimping and mechanical fasteners, may also be employed. The distal end of the malleable mandrel 116 is secured to a tip member 120. The exemplary tip member 120 is provided with a suture aperture 121 (or a suture groove). If desired, physicians may pass a suture through the aperture 121 (or around a suture groove) and use the suture to pull the shaft 102 around a body structure.

The handle 104 is configured to be gripped by the physician and used to press the shaft distal portion 114 and electrodes 106 against tissue. To that end, the exemplary handle 104 is also about 7 to 18 cm in length and about 2 to 5 cm around its perimeter (measured perpendicularly to the longitudinal axis), which is suitable for gripping by the physician.

The exemplary surgical probe component 100 is a fluid cooled surgical probe and, as illustrated in FIG. 3, the electrically non-conductive outer structure 118 includes fluid inlet and outlet lumens 122 and 124, power and signal wire lumens 126 and 128, a central lumen 130 for the mandrel 116. To that end, the tip member 120 includes a connection lumen (not shown) that connects the inlet lumen 122 to the outlet lumen 124, as well as a pair of plugs (not shown) to seal the power and signal wire lumens 126 and 128. Heat from the electrodes 106 is transferred through the outer structure 118 to fluid that is flowing through the inlet and outlet lumens 122 and 124. Accordingly, in addition to being electrically non-conductive, the material used to form the outer structure 118 should be relatively high in thermal conductivity. As used herein, "relatively high" thermal conductivity is at least about 1 W/m·K and preferably ranges from about 1 to about 10 W/m·K. Suitable electrically non-conductive, thermally conductive thermoplastics for the outer structure 118 include flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France.

In addition to the aforementioned fillers, heat transfer may be promoted by minimizing the thickness of the electrically non-conductive material between the lumens 122 and 124 and the electrodes 106 and by maximizing the cross-sectional area of the inlet and outlet lumens. With respect to the outer structure 118 illustrated in FIG. 3, for example, in an implementation where the outer diameter of the outer structure is about 8 French (2.66 mm), the thickness of the outer wall 132 between the electrodes 106 and the inlet and outlet lumens 122 and 124 will be about 0.08 mm to about 0.36 mm. It should be noted that when the outer wall thickness is about 0.02 mm or less, materials with less than "relatively high" thermal conductivities, such as Pebax® material and polyurethane, may also be used for the outer structure 118.

Suitable materials for the malleable hypotube 110 include annealed stainless steel, while the suitable material for the mandrel 116 includes annealed stainless steel and beryllium copper.

As illustrated for example in FIGS. 1-4, fluid may be supplied to the surgical probe component 100 by way of an infusion tube 134, which is connected to the inlet lumen 122. The infusion tube 134 extends through an aperture 135 in the handle 104 and is provided with stop-cock, which may be connected to a fluid supply and control apparatus 300 in the manner described below with reference to FIG. 13. Similarly, a ventilation tube 136 is connected to the outlet lumen 124 and extends through an aperture 137 in the handle 104. The ventilation tube 136 also includes a stopcock that may be connected to the fluid supply and control apparatus.

The electrodes 106 in the exemplary probe component 100 illustrated in FIGS. 1-4 are electrically coupled to individual power wires 138 that pass from the power wire lumen 126, and through a power wire tube 140, to an electrical connector 141 that is associated with a slot 142 in the handle 104. Suitable electrical connectors include PC boards, edge card connectors, subminiature D connectors, ribbon cable connectors, and pin and socket connectors. A plurality of temperature sensors 144, such as thermocouples or thermistors, may be located on, under, abutting the longitudinal end edges of, or in between, the electrodes 106. A reference thermocouple (not shown) may also be provided. In the exemplary implementation, temperature sensors 144 are located at both longitudinal ends of each electrode 106. The temperature sensors 144 are connected to the electrical connector 141 by signal wires 146, which pass through the signal wire lumen 128 and a signal wire tube 148. The temperature sensors 144 are also located within a linear channel 150 that is formed in the non-conductive outer structure 118. The linear channel 150 insures that the temperature sensors will all face in the same direction (e.g. facing tissue) and be arranged in linear fashion.

The number of electrodes carried on the shaft distal portion 114 will typically depend upon the number of power connections available on the ESU and common electrical connector 141 (e.g. a PC board) as well as the number and purpose of the electrodes carried by the clamp component 200. In the exemplary implementation, the clamp component 200 includes two electrodes that are used to transmit energy and one that is used to return energy when operating in a bipolar mode, as is discussed below with reference to FIGS. 8-12. In those instances where the ESU and common electrical connector 141 are configured for seven electrodes and two temperature sensors for each transmitting electrode, the probe component 100 will include five spaced electrodes 106.

The spaced electrodes 106 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 106 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Still other types of electrodes are formed from electroless plated copper on a polyimide film or tubular substrate. Gold, nickel or silver should be plated over the copper for electrochemical stability and improved biocompatibility. The plating can be applied in continuous form (up to about 1-2 cm in length at most) or can be applied in a pattern that is designed to improve current density distributions and/or electrode flexing characteristics. Temperature sensors (e.g. thermocouples) may be incorporated into the electrode structure by placing the temperature sensors in a channel in the polyimide film or tubular substrate and then plating over them.

The exemplary flexible electrodes 106 are preferably about 4 mm to about 20 mm in length. In the preferred embodiments, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

Additional details concerning fluid cooled surgical probes similar to that described above are presented in U.S. patent application Pub. No. 2003/0078644, which is entitled "Apparatus for Supporting Diagnostic and Therapeutic Elements in Contact With Tissue Including Dual Lumen Cooling Device" and incorporated herein by reference.

Although the exemplary surgical probe component 100 is an internally cooled, fluid cooled surgical probe, the present inventions are not limited to such probes. Other exemplary surgical probes include, for example, externally cooled, fluid cooled surgical probes such as those illustrated in U.S. patent application Pub. No. 2003/0014048, which is entitled "Fluid Cooled Apparatus for Supporting Diagnostic and Therapeutic Elements in Contact with Tissue" and non-cooled surgical probes such as those illustrated in U.S. Pat. No. 6,645,200. The exemplary surgical probe component 100 may also be replaced with a catheter component in those instances where percutaneous access (e.g. access through the femoral vein to a chamber within the heart) is desired. Suitable catheters are disclosed in U.S. Pat. Nos. 6,013,052, 6,203,525, 6,214,002 and 6,241,754. The U.S. patents and published applications mentioned in this paragraph are incorporated herein by reference.

Turning to the clamp component, the exemplary clamp component 200 illustrated in FIG. 1 is configured such that it may be removably secured to a clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

One example of a clamp to which the clamp component 200 may be secured is generally represented by reference numeral 202 in FIGS. 5-7. The clamp 202 includes a pair of rigid arms 204 and 206 that are pivotably connected to one another by a pin 208. The proximal ends of the arms 204 and 206 are respectively connected to a pair of handle members 210 and 212, while the distal ends are respectively connected to a pair of clamp members 214 and 216. The clamp members 214 and 216 may be rigid or malleable and, if rigid, may be linear or have a pre-shaped curvature. A locking device 218 locks the clamp in the closed orientation, and prevents the clamp members 214 and 216 from coming any closer to one another than is illustrated in FIG. 5, thereby defining a predetermined spacing between the clamp members. The clamp 202 is also configured for use with a pair of soft, deformable inserts (not shown) that may be removably carried by the clamp members 214 and 216 and allow the clamp to firmly grip a bodily structure without damaging the structure. To that end, the clamp members 214 and 216 each include a slot 220 (FIGS. 6 and 7) that is provided with a sloped inlet area 222 and the inserts include mating structures that are removably friction fit within the slots. The exemplary clamp component 200 may be mounted on the clamp members in place of the inserts.

With respect to clamp component itself, the clamp component 200 in the exemplary hybrid lesion formation apparatus 10 illustrated in FIG. 1 includes a first energy transmission device 224 that may be connected to one of the clamp members 214 and 216 (FIGS. 5 and 13) and a second energy transmission device 226 that may be connected to the other. The energy transmission devices 224 and 226 are respectively carried on support structures 228 and 230, which are connected to a cable 232 by a molded junction 234. The cable 232 enters the handle 104 and, preferably, enters the handle just proximally of the strain relief element 107.

Although clamp components in accordance with the present invention may be operated in bipolar and unipolar modes, the exemplary clamp component 200 is configured so as to be especially useful in a bipolar mode wherein the first energy transmission device 224 will transmit energy through tissue to the second energy transmission device 226. To that end, and as illustrated for example in FIGS. 8-12, the first energy transmission device 224 includes a pair of electrodes 236 and 238 that may be independently controlled, while the second energy transmission device 226 includes a single electrode 240. Such an arrangement provides for higher fidelity control of the overall region that is transmitting energy and a gap free, constant potential region on the return side.

The first and second energy transmission devices 224 and 226 in the illustrated embodiment illustrated in FIGS. 8-12 are also provided with respective mounting devices 242 that may be used to mount the clamp component 200 in general, and the energy transmission devices in particular, on the clamp 202. Additionally, although the configuration of the clamp component 200 may vary from application to application to suit particular situations, the exemplary clamp component is configured such that the electrodes 236 and 238 will be parallel to, and relatively close to one another (i.e. a spacing of about 1-10 mm), the electrode 240 when the clamp 202 is in the closed orientation. Such an arrangement will allow the clamp component 200 to grip a bodily structure without cutting through the structure.

Referring more specifically to FIGS. 9 and 11, each mounting device 242 includes a base member 246 that has a groove 248 which is configured to receive the support structure 228 and electrodes 236 and 238 (or support structure 230 and electrode 240). About 20% of the electrode surface (i.e. about 75° of the 360° circumference) is exposed in the illustrated embodiment. Adhesive may be used to hold the support structures and electrodes in place. The mounting device also includes a connector 250 that is configured to removably mate with the clamp slot 220 (FIGS. 6 and 7). The exemplary connector 250 is provided with a relatively thin portion 252 and a relatively wide portion 254, which may consist of a plurality of spaced members (as shown) or an elongate unitary structure, in order to correspond to the shape of the slot 220.

The exemplary energy transmission devices 224 and 226 may also include a wettable fluid retention element 256 that is saturated with ionic fluid (such as saline) prior to use. Suitable materials for the fluid retention elements 256 include biocompatible fabrics commonly used for vascular patches (such as woven Dacron®), open cell foam materials, hydrogels, nanoporous balloon materials (with very slow fluid delivery to the surface), and hydrophilic nanoporous materials. The effective electrical resistivity of the fluid retention element 256 when wetted with 0.9% saline (normal saline) should range from about 1 $\Omega$-cm to about 2000 $\Omega$-cm. A preferred resistivity for epicardial and endocardial procedures is about 1000 $\Omega$-cm. Alternatively, one or both of the fluid retention elements may be removed so that the electrodes contact the tissue directly.

The electrodes 236 and 238 in the exemplary clamp component illustrated in FIGS. 8-12 are connected to power wires 258, while the electrode 240 is connected to a power wire 260. The power wires 258 and 260 extend through the support structures 228 and 230, respectively, as well as the cable 232, and into the handle 104. The power wires 258 are connected to the electrical connector 141 (FIGS. 1 and 4) that is associated with the slot 142 in the handle 104. As such, the electrodes 236 and 238 and associated power wires 258 from the clamp component 200 are connected to the same electrical connector as the power wires 138 from the probe component 100. Conversely, the power wire 260 extends through a cable 266 (FIG. 1), which enters the proximal end of the handle 104 through an aperture 267, to a connector 268 so that the electrode 240 may be connected to one of the power return ports 340 on the ESU 322 (FIG. 13).

A plurality of temperature sensors 262 (FIG. 11), such as thermocouples or thermistors, may be located on, under, abutting the longitudinal end edges of, or in between, the electrodes 236 and 238. A reference thermocouple (not shown) may also be provided. In the exemplary implementation, temperature sensors 262 are located at both longitudinal ends of each of the electrodes 236 and 238. The temperature sensors 262 are connected to the electrical connector 141 by signal wires 264, which pass through the support structure 228 and cable 232. In other words, the signal wires 264 from the clamp component 200 are connected to the same electrical connector 141 (a PC board in the exemplary embodiment) as the signal wires 146 from the probe component 100. The temperature sensors 262 are also located within a linear channel 263 that is formed in the support structure 228. The linear channel insures that the temperature sensors will all face in the same direction (e.g. facing tissue) and be arranged in linear fashion.

With respect to dimensions and materials, the support structures 228 and 230 are flexible tubular structures which have an outer diameter that is, depending on the diameter of the electrodes 236, 238 and 240, typically between about 1.5 mm and about 3 mm. The support structures 228 and 230 in the illustrated embodiment, which are intended for use in cardiovascular applications, have an outer diameter of about 2 mm. Suitable support structure materials include, for example, flexible biocompatible thermoplastic tubing such as unbraided Pebax® material, polyethylene, or polyurethane tubing.

The mounting devices 242 are preferably formed from polyurethane. The length of the mounting devices 242 will vary according to the intended application. In the area of cardiovascular treatments, it is anticipated that suitable lengths will range from, but are not limited to, about 4 cm to about 10 cm. In the exemplary implementation, the base members 242 are about 6 cm in length.

A variety of other suitable clamp based energy transmission devices that may be incorporated into hybrid lesion formation apparatus in accordance with the present inventions are illustrated in U.S. patent application Pub. No. 2003/0158547, which is entitled "Apparatus for Converting a Clamp Into an Electrophysiology Device" and is incorporated herein by reference.

III. Exemplary Systems

A tissue coagulation system 1000 in accordance with one embodiment of a present invention is illustrated in FIG. 13. The exemplary system 1000 includes the hybrid lesion formation apparatus 10, a fluid supply and control apparatus 300 and a power supply and control apparatus 320. In addition, the clamp component 200 is mounted on the clamp 202 to form a clamp-based tissue coagulation device.

The fluid supply and control apparatus 300, which may be used to supply cooling fluid to the surgical probe component 100, includes housing 302, a fluid outlet port 304, and a fluid inlet port 306. The fluid outlet port 304 may be coupled to the stopcock or other connector associated with the infusion tube 134 (and, therefore, to the inlet lumen 122) by a connector tube 308, while the fluid inlet port 306 may be coupled to the stopcock or other connector associated with the ventilation tube 136 (and, therefore, to the outlet lumen 124) by a connector tube 310. An infusion pump capable of variable flow rates is one example of a suitable fluid supply and control apparatus.

The cooling fluid is not limited to any particular fluid. Preferably, however, the fluid will be a low or electrically non-conductive fluid such as sterile water or 0.9% saline solution in those instances where the fluid will not be used to transmit current to tissue. A suitable fluid inlet temperature is about 0 to 25° C. and the fluid supply and control apparatus 300 may be provided with a suitable cooling system, if desired, to bring the temperature of the fluid down to the desired level. In a five electrode embodiment where 150 W is being supplied to the electrodes 106, for example, a suitable constant fluid flow rate is about 5 ml/min to about 20 ml/min.

The power supply and control apparatus 320 includes an electrosurgical unit ("ESU") 322 that supplies and controls RF power. A suitable ESU is the Model 4810A ESU sold by Boston Scientific Corporation of Natick, Mass., which is capable of supplying and controlling power on an electrode-by-electrode basis. This is sometimes referred to as "multi-channel control." Typically, power will be controlled as a function of the temperature at each electrode in order to insure that tissue is coagulated without over-heating and causing coagulum and charring. With respect to temperature sensing, temperature at the electrodes 106 on the surgical probe component 100, as well as the electrodes 236 and 238 on the clamp component 200, is measured by the aforementioned temperatures sensors 144 and 262. Alternatively, in those instances where temperature sensors are not employed, the respective temperatures at each electrode 106, 236 and 238 may be determined by measuring impedance at each electrode.

The power and signal wires 138, 146, 258 and 264 should be connected to the electrical connector 141 in such a manner that the physician will know in advance which of the ESU control channels correspond to the five electrodes 106 on the probe component 100 and which of the ESU control channels correspond the electrodes 236 and 238 on the clamp component 200. In one exemplary configuration, control channels 1 and 2 may be used for the clamp component electrodes 236 and 238 and control channels 3-7 may be used for the five probe component electrodes 106.

The ESU 322 transmits energy to the electrodes 106, 236 and 238 by way of a cable 324. The cable 324 includes a connector 326, which may be connected to the electrical connector 141 in the probe handle 104, and a connector 328, which may be connected to a power output port 330 on the ESU 322.

Tissue coagulation energy emitted by the electrodes 106 is returned to the ESU 322 through an indifferent electrode 334 that is externally attached to the skin of the patient with a patch, or one or more electrodes (not shown) that are positioned in the blood pool, and a cable 336. The cable 336 includes a connector 338 that may be connected to one of the power return ports 340 on the ESU 322. Similarly, tissue coagulation energy emitted by the electrode 236 and 238 on the energy transmission device 224 is returned to the ESU 322 by way of the electrode 240 on the energy transmission device 226, the power wires 260 and the cable 266. The cable 326 is connected to the other ESU power return port 340 by the connector 268. Preferably, the ESU power output port 330 and corresponding connector 328 have different configurations than the power return port 340 and corresponding connectors 268 and 338 in order to prevent improper connections.

The exemplary tissue coagulation system 1000 illustrated in FIG. 13 may be used to form a variety of lesions in a variety of anatomical structures. By way of example, but not limitation, the tissue coagulation system 1000 may be used in the following manner to form lesions in myocardial tissue to cure atrial fibrillation.

After the clamp component 200 has been secured to the clamp 202 and the hybrid lesion formation apparatus 10 has been connected to the ESU 322 by the connectors 328 and 368, the clamp 202 may be used to position the clamp component energy transmission devices 224 and 226 on left atrial tissue adjacent to opposite sides of the right pulmonary vein pair. The clamp members 214 and 216 may then be brought into a completely closed orientation or, depending on the tissue structure, a slightly open orientation so long as the pulmonary veins are firmly held. The ESU 322 is used to supply coagulation energy to the electrodes 236 and 238, and energy is returned to the ESU by way of the electrode 240. Energy will be continued to be supplied in a controlled manner based on the temperatures monitored by the temperature sensors 262 until a transmural epicardial lesion around the right pulmonary vein pair is formed. This process is then repeated on the left pulmonary vein pair. It should be noted, however, that individual lesions may be formed around each of the pulmonary veins instead of around the pulmonary vein pairs. The clamp component 200 and clamp 202 may then be placed on the sterile drape covering the patient, where it can remain until the ablation procedure is completed.

The surgical probe component 100 of the hybrid lesion formation apparatus 10 may then be used, if necessary, to touch up the lesions formed by the clamp component 200. As noted above, this may be accomplished without disconnecting the clamp component 200 from the ESU 322 and then connecting surgical probe component 100 to the ESU because both components share the electrical connector 141 in the handle 104. Tissue coagulation energy from the ESU 322 will be supplied to one, some or all of the electrodes 106 and returned to the ESU by way of the indifferent electrode 334. The surgical probe component 100 may also be used to create a linear transmural epicardial lesion between the right and left pulmonary vein pairs and/or a linear transmural lesion that extends from the lesion between the right and left pulmonary vein pairs to the left atrial appendage.

Although the inventions disclosed herein have been described in terms of the preferred embodiments above, numerous modifications and/or additions to the above-described preferred embodiments would be readily apparent to one skilled in the art.

By way of example, but not limitation, the electrical connector 141 may be located at the end of a cable that extends outwardly from the handle, instead of within the handle, so that the cable 324 may be eliminated.

Figure 14:
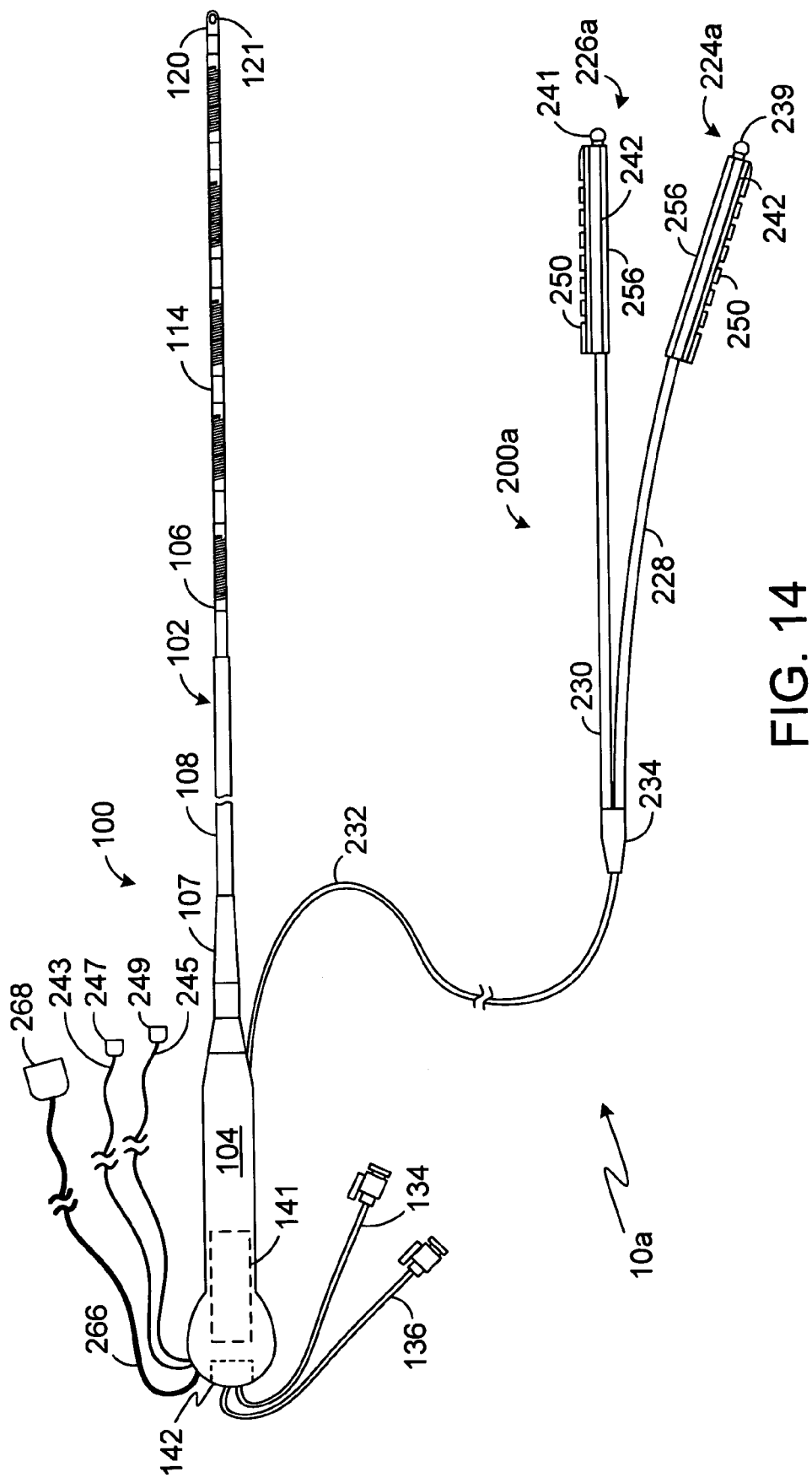
FIG. 14 is a plan view of a hybrid lesion formation apparatus in accordance with a preferred embodiment of a present invention.

Turning to FIG. 14, the clamp component 200a in the exemplary hybrid lesion formation apparatus 10a, which is otherwise identical to the hybrid lesion formation apparatus 10, is provided with tissue stimulation (or "pacing") electrodes 239 and 241 on the energy transmission devices 224a and 226a. The tissue stimulation electrodes 239 and 241 are carried on the ends of the support structures 228 and 230. The tissue stimulation electrodes 239 and 241 are also connected to signal lines 243 and 245, which extend through the support structures 228 and 230 and cable 232, as well as through the proximal end of the handle 104, to connectors 247 and 249. This allows the tissue stimulation electrodes 239 and 241 to be connected to a conventional pacing apparatus, such as the Medtronic Model Nos. 5330 and 5388 external pulse generators, or to an ECG machine that is capable of monitoring and recording electrical impulses.

The tissue stimulation electrodes 239 and 241 may then be used to supply a bipolar pacing pulse (e.g. about 20 mA) on the side opposite the left atrium of a lesion formed with the hybrid lesion formation apparatus 10a. The physician can determine whether or not a therapeutic lesion (or "complete block") has been formed by observing the left atrium. If the pacing pulse is able to cross the lesion, the heart will beat faster (e.g. 120 beats/minute). This may be determined by observation or by use of an ECG machine that is monitoring the heart. Here, additional coagulation will be required to complete the lesion. The failure to stimulate the heart from the side of the lesion opposite the left atrium is, on the other hand, indicative of the formation of a therapeutic lesion. Nevertheless, because muscle bundles are not always connected near the pulmonary veins, it is preferable that the stimulation energy be applied to a number of tissue areas on the side of the lesion opposite the left atrium to reduce the possibility of false negatives. Alternatively, the tissue stimulation electrodes 239 and 241 may be used to monitor tissue within the region that was intended to be isolated. In the context of pulmonary vein isolation, for example, the tissue stimulation electrodes 239 and 241 may be placed in contact with viable tissue on the pulmonary vein side of the lesion.

Additional information concerning tissue stimulation electrodes, as well as the manner in which they may be employed in conjunction with a clamp based device, is provided in U.S. application Ser. No. 10/727,143, which is entitled "Surgical Methods And Apparatus For Forming Lesions In Tissue And Confirming Whether A Therapeutic Lesion Has Been Formed" and incorporated herein by reference.

It is intended that the scope of the present inventions extend to all such modifications and/or additions and that the scope of the present inventions is limited solely by the claims set forth below.

We claim:

1. A lesion formation apparatus, comprising:
   a probe component including a shaft, at least one energy transmission device on an outer portion of the shaft, and an electrical connector operably connected to the at least one energy transmission device; and
   a clamp component including a first clamp member and a second clamp member that are pivotably connected to each other, the clamp component being tethered to the probe component by an electrical cable and including at least one energy transmission device operably connected to the probe component electrical connector by the electrical cable.

2. An apparatus as claimed in claim 1, wherein the probe component comprises a surgical probe component.

3. An apparatus as claimed in claim 1, wherein the probe component shaft comprises a relatively short, relatively stiff shaft.

4. An apparatus as claimed in claim 1, wherein the at least one probe component energy transmission device comprises an electrode.

5. An apparatus as claimed in claim 1, wherein the at least one probe component energy transmission device comprises a plurality of spaced energy transmission devices.

6. An apparatus as claimed in claim 1, wherein the probe component includes a handle and the electrical connector is located at least partially within the handle.

7. An apparatus as claimed in claim 1, wherein the clamp component includes first and second support structures and the at least one clamp component energy transmission device comprises first and second energy transmission devices respectively carried on the first and second support structures.

8. An apparatus as claimed in claim 1, wherein the probe component includes a temperature sensor associated with the at least one energy transmission device and connected to the electrical connector.

9. An apparatus as claimed in claim 1, wherein the clamp component includes a temperature sensor associated with the at least one energy transmission device and connected to the electrical connector.

10. An apparatus as claimed in claim 1, wherein the electrical connector comprises a PC board.

11. The apparatus as claimed in claim 1, wherein the probe component and the clamp component are separate devices connected by the probe component electrical connector.

12. The apparatus as claimed in claim 11, wherein the probe component and the clamp component are independently controllable.

13. The lesion formation apparatus of claim 1, wherein the probe component is a tubular structure having a proximal end and a distal end, the distal end defining a suture aperture.

14. The lesion formation apparatus of claim 1, wherein the electrical cable is flexible, and the probe component and the clamp component are movable relative to each other while tethered to each other by the flexible electrical cable.

15. A lesion formation apparatus, comprising:
   a probe component including a shaft, at least one energy transmission device on the shaft, and an electrical connector operably connected to the at least one energy transmission device; and a clamp component including at least one energy transmission device operably connected to the probe component electrical connector, wherein the at least one clamp component energy transmission device comprises first and second energy transmission devices and the clamp component includes a first mounting device configured to mount the first energy transmission device on a first clamp member and a second mounting device configured to mount the second energy transmission device on a second clamp member.

16. A lesion formation apparatus, comprising:
a probe component including a shaft, at least one energy transmission device on the shaft, and an electrical connector operably connected to the at least one energy transmission device; and
a clamp component including at least one energy transmission device operably connected to the probe component electrical connector, wherein the at least one clamp component energy transmission device comprises first and second energy transmission devices and the first energy transmission device is connected to the electrical connector and the second energy transmission is not connected to the electrical connector.

17. A lesion formation apparatus for use with a source of tissue coagulation energy, the source of tissue coagulation energy including a power output port and a power return port, the lesion formation apparatus comprising:
a tissue coagulation probe including a shaft and an energy transmission device carried on an outer portion of the shaft;
a bipolar tissue coagulation device including first and second energy transmission devices;
first connector means comprising a cable for facilitating connection of the energy transmission device on the tissue coagulation probe and the first energy transmission device on the bipolar tissue coagulation device to the power output port; and
second connector means for connecting the second energy transmission device on the bipolar tissue coagulation device to the power return port.

18. An apparatus as claimed in claim 17, wherein the tissue coagulation probe shaft comprises a relatively short, relatively stiff shaft.

19. An apparatus as claimed in claim 17, wherein the tissue coagulation probe energy transmission device comprises an electrode.

20. An apparatus as claimed in claim 17, wherein the tissue coagulation probe energy transmission device comprises a plurality of spaced energy transmission devices and the first connector means facilitates connection of the plurality of spaced energy transmission devices to the power output port.

21. An apparatus as claimed in claim 17, further comprising: a second cable adapted to connect the first connector means to the energy output port.

22. The apparatus as claimed in claim 17, wherein the tissue coagulation probe and the bipolar tissue coagulation device are separate devices.

23. The apparatus as claimed in claim 22, wherein the tissue coagulation probe and the bipolar tissue coagulation device are independently controllable.

24. A lesion formation apparatus for use with a source of tissue coagulation energy, the source of tissue coagulation energy including a power output port and a power return port, the lesion formation apparatus comprising:
a tissue coagulation probe including a shaft and an energy transmission device carried on the shaft;
a bipolar tissue coagulation device including first and second energy transmission devices;
first connector means for facilitating connection of the energy transmission device on the tissue coagulation probe and the first energy transmission device on the bipolar tissue coagulation device to the power output port; and
second connector means for connecting the second energy transmission device on the bipolar tissue coagulation device to the power return port, wherein the bipolar tissue coagulation device includes a first mounting device for mounting the first energy transmission device to a first clamp member and a second mounting device for mounting the second energy transmission device to a second clamp member.

25. A lesion formation system, comprising:
a source of tissue coagulation energy including an energy output port and an energy return port;
a lesion formation apparatus including
a probe component including a shaft, at least one energy transmission device on an outer portion of the shaft, and an electrical connector operably connected to the at least one energy transmission device; and
a clamp component including a first clamp member and a second clamp member that are pivotably connected to each other, the clamp component being tethered to the probe component by an electrical cable and including a first energy transmission device operably connected to the probe component electrical connector by the electrical cable, a second energy transmission device, and an electrical connector operably connected to the second energy transmission device and adapted to be connected to the energy return port.

26. A system as claimed in claim 25, further comprising: a second cable that connects the probe component electrical connector to the energy output port.

27. A system as claimed in claim 25, the probe component shaft comprises a relatively short, relatively stiff shaft.

28. A system as claimed in claim 25, wherein the at least one probe component energy transmission device comprises a plurality of spaced energy transmission devices.

29. A system as claimed in claim 25, wherein the probe component includes a handle and the probe component electrical connector is located at least partially within the handle.

30. A system as claimed in claim 25, wherein the clamp component includes first and second support structures and the at least one clamp component energy transmission device comprises first and second energy transmission devices respectively carried on the first and second support structures.

31. The system as claimed in claim 25, wherein the probe component and the clamp component are separate devices connected by the probe component electrical connector.

32. The system as claimed in claim 31, wherein the probe component and the clamp component are independently controllable.

33. The lesion formation apparatus of claim 25, wherein the probe component is a tubular structure having a proximal end and a distal end, the distal end defining a suture aperture.

34. The lesion formation apparatus of claim 25, wherein the electrical cable is flexible, and the probe component and the clamp component are movable relative to each other while tethered to each other by the flexible electrical cable.

35. A lesion formation system, comprising:
a source of tissue coagulation energy including an energy output port and an energy return port;
a lesion formation apparatus including a probe component including a shaft, at least one energy transmission device on the shaft, and an electrical connector operably connected to the at least one energy transmission device; and a clamp component including a first energy transmission device operably connected to the probe component electrical connector, a second energy transmission device, and an electrical connector operably connected to the second energy transmission device and adapted to be connected to the energy return port, wherein at least one clamp component energy transmission device comprises first and second energy transmission devices and the clamp component includes a first mounting device configured to mount the first energy transmission device on a first clamp member and a second mounting device configured to mount the second energy transmission device on a second clamp member.

36. A lesion formation method, comprising:

simultaneously connecting at least one energy transmission device on an outer portion of a shaft of a tissue coagulation probe and a clamp-based tissue coagulation device to the same power output port of a source of tissue coagulation energy, the clamp-based tissue coagulation device being tethered to the tissue coagulation probe by an electrical cable and including a first clamp member and a second clamp member that are pivotably connected to each other.

37. A lesion formation method as claimed in claim 36, further comprising:

positioning the clamp-based tissue coagulation device adjacent to tissue; and supplying tissue coagulation energy to the clamp-based tissue coagulation device to form a lesion.

38. A lesion formation method as claimed in claim 37, wherein positioning the clamp-based tissue coagulation device comprises positioning the clamp-based tissue coagulation device around at least one pulmonary vein.

39. A lesion formation method as claimed in claim 36, further comprising:

connecting the clamp-based tissue coagulation device to a power return port on the source of tissue coagulation energy;

positioning the clamp-based tissue coagulation device adjacent to tissue;

supplying tissue coagulation energy to a portion of the clamp-based tissue coagulation device to form a lesion; and returning tissue coagulation energy to the source of tissue coagulation energy by way of another portion of the clamp-based tissue coagulation device.

40. A lesion formation method as claimed in claim 36, further comprising:

positioning the tissue coagulation probe adjacent to tissue; and supplying tissue coagulation energy to the tissue coagulation probe to form a lesion.

41. The method as claimed in claim 36, wherein the tissue coagulation probe and the clamp-based tissue coagulation device are separate devices.

42. The method as claimed in claim 41, wherein the tissue coagulation probe and the clamp-based tissue coagulation device are independently controllable.

43. The method as claimed in claim 36, simultaneously connecting further comprising simultaneously connecting the tissue coagulation probe and the clamp-based tissue coagulation device to the same power output on a radiofrequency source of tissue coagulation energy.

44. The method as claimed in claim 36, further comprising, prior to simultaneously connecting:

providing a tissue coagulation probe; and providing a clamp-based tissue coagulation device that is separated from the tissue coagulation probe and electrically connected to the tissue coagulation probe by a common electrical connector, simultaneously connecting further comprising simultaneously connecting the tissue coagulation probe and the clamp-based tissue coagulation device to the same power output port with the common electrical connector.

45. The lesion formation apparatus of claim 36, wherein the probe component is a tubular structure having a proximal end and a distal end, the distal end defining a suture aperture.

46. A lesion formation apparatus, comprising:

a probe component including a shaft, at least one energy transmission device on an outer portion of the shaft, and an electrical connector operably connected to the at least one energy transmission device; and a clamp component tethered to the probe component by an electrical cable, the clamp component including a first support structure carrying a first energy transmission device and a second support structure carrying a second energy transmission device, at least one of the first and second energy transmission devices being operably connected to the probe component electrical connector by the electrical cable.

47. A lesion formation system, comprising:

a source of tissue coagulation energy including an energy output port and an energy return port; and a lesion formation apparatus including a probe component including a shaft, at least one energy transmission device on an outer portion of the shaft, and an electrical connector operably connected to the at least one energy transmission device, and a clamp component tethered to the probe component by an electrical cable, the clamp component including a first support structure carrying a first energy transmission device that is operably connected to the probe component electrical connector by the electrical cable, a second support structure carrying a second energy transmission device, and an electrical connector operably connected to the second energy transmission device and adapted to be connected to the energy return port.

* * * * *